United States Patent
Winter et al.

(10) Patent No.: US 12,083,037 B2
(45) Date of Patent: Sep. 10, 2024

(54) MANDIBULAR ADVANCEMENT DEVICE AND METHOD OF ADJUSTING A DIMENSION OF A COUPLING ASSEMBLY OF A MANDIBULAR ADVANCEMENT DEVICE

(71) Applicant: KONINKLIJKE PHILIPS N.V., Eindhoven (NL)

(72) Inventors: Stefan Winter, Würselen (DE); Koray Karakaya, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 54 days.

(21) Appl. No.: 16/466,082

(22) PCT Filed: Dec. 6, 2017

(86) PCT No.: PCT/EP2017/081617
§ 371 (c)(1),
(2) Date: Jun. 3, 2019

(87) PCT Pub. No.: WO2018/104358
PCT Pub. Date: Jun. 14, 2018

(65) Prior Publication Data
US 2019/0350749 A1   Nov. 21, 2019

Related U.S. Application Data

(60) Provisional application No. 62/430,382, filed on Dec. 6, 2016.

(51) Int. Cl.
*A61F 5/56* (2006.01)
(52) U.S. Cl.
CPC .................................. *A61F 5/566* (2013.01)

(58) Field of Classification Search
CPC .. A61F 5/56; A61F 5/566; A61F 2002/30991; A61F 2005/563;
(Continued)

(56) References Cited

U.S. PATENT DOCUMENTS 4,795,342 A    1/1989  Jones
5,829,975 A *  11/1998 Gold ........................ A61C 7/36
                                                    433/19
(Continued)

FOREIGN PATENT DOCUMENTS

EP        1972311 A1      9/2008
KR    20130045285 A       5/2013
(Continued)

OTHER PUBLICATIONS

Li et al., Integration of Hydrogels with Hard and Soft Microstructures, 2007, Journal of Nanoscience and Nanotechnology, vol. 7, p. 786. (Year: 2007).*

(Continued)

*Primary Examiner* — Alireza Nia
*Assistant Examiner* — Michael Milo (57) ABSTRACT

A mandibular advancement device (102,302) includes a first brace member (104,304) structured to engage an upper dentition of a user, a second brace member (106,306) structured to engage a lower dentition of a user, and a number of coupling assemblies (108,308) each coupling the first brace member to the second brace member. Each of the number of coupling assemblies includes an actuating element (114,314) structured to automatically adjust a dimension (136,336) of the coupling assembly. The actuating element is selected from the group consisting of a biasing element (114) and a volume responsive material (314).

4 Claims, 6 Drawing Sheets

(58) Field of Classification Search
CPC ... A61F 2/2803; A61B 5/1072; A61B 5/1076; A61B 5/4557; A61B 5/481; A61B 5/4818; A61B 5/097; A61B 5/4812; A61B 17/8071; A63B 71/085; A63B 2071/086; A61C 19/045; A61C 11/00; A61C 7/08; A61C 7/36; A61C 9/0006; Y10S 602/902
USPC .......................... 128/848, 859, 861; 602/902
See application file for complete search history.

(56) References Cited

U.S. PATENT DOCUMENTS

| | | | |
|---|---|---|---|
| 6,273,859 B1 | 8/2001 | Remmers et al. | |
| 8,578,937 B2 | 11/2013 | Bhat et al. | |
| 10,219,935 B2 | 3/2019 | Hadas | |
| 2005/0028826 A1* | 2/2005 | Palmisano | A61F 5/566 128/848 |
| 2011/0000495 A1* | 1/2011 | Ash | A61F 5/566 128/848 |
| 2014/0057222 A1* | 2/2014 | Kumar | A61C 7/20 433/19 |
| 2014/0248575 A1* | 9/2014 | Desouches | A61C 7/36 433/19 |
| 2014/0255866 A1* | 9/2014 | Faust | A61C 7/20 433/24 |
| 2016/0022205 A1 | 1/2016 | Remmers et al. | |
| 2016/0199215 A1* | 7/2016 | Kopelman | A61F 5/566 128/848 |
| 2016/0220331 A1 | 8/2016 | Johnston | |
| 2016/0324681 A1* | 11/2016 | Flanagan | A61F 5/566 |
| 2018/0228644 A1* | 8/2018 | Shin | A61F 5/566 |

FOREIGN PATENT DOCUMENTS

| | | | | |
|---|---|---|---|---|
| WO | 2007014429 A1 | | 2/2007 | |
| WO | WO-2007075928 A2 * | | 7/2007 | ......... A61B 5/1486 |
| WO | WO-2017135907 A1 * | | 2/2016 | ............. A61F 5/566 |
| WO | WO-2016131827 A1 * | | 8/2016 | ......... A61C 13/0019 |

OTHER PUBLICATIONS

Eddington, David T., and David J. Beebe. "Flow control with hydrogels." Advanced drug delivery reviews 56.2 (2004): 199-210.
Westbrook, Kristofer K., and H. Jerry Qi. "Actuator designs using environmentally responsive hydrogels." Journal of intelligent material systems and structures (2007).
International Search Report and Written Opinion, International Application No. PCT/EP2017/081617, Mailed May 30, 2018.

* cited by examiner

Prior Art

MANDIBULAR ADVANCEMENT DEVICE AND METHOD OF ADJUSTING A DIMENSION OF A COUPLING ASSEMBLY OF A MANDIBULAR ADVANCEMENT DEVICE

CROSS-REFERENCE TO PRIOR APPLICATIONS

This application is the U.S. National Phase application under 35 U.S.C. § 371 of International Application Serial No. PCT/EP2017/081617, filed on 6 Dec. 2017, which claims the benefit of U.S. Application Ser. No. 62/430,382, filed on 6 Dec. 2016. These applications are hereby incorporated by reference herein.

BACKGROUND OF THE INVENTION

1. Field of the Invention

The present invention relates to mandibular advancement devices. The present invention also relates to methods of adjusting dimensions of coupling assemblies of mandibular advancement devices.

2. Description of the Related Art

It is well known that many individuals suffer from disordered breathing during sleep. Obstructive sleep apnea (OSA), which affects millions of people throughout the world, is a common example of such disordered breathing. OSA is a condition in which sleep is repeatedly interrupted by an inability to breathe. This inability to breathe is typically caused by intermittent obstruction of a person's airway. Obstruction of the airway is believed to be due, at least in part, to a general relaxation of the muscles which stabilize the upper airway segment. When these muscles relax, the surrounding tissues collapse thereby obstructing the airway.

Those afflicted with OSA experience sleep fragmentation and intermittent cessation of ventilation during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of OSA include right ventricular dysfunction, carbon dioxide retention during sleep, as well as wakefulness, and continuous reduced arterial oxygen tension. Sleep apnea sufferers may be at risk for excessive mortality from these factors as well as by an elevated risk for accidents while driving and/or operating potentially dangerous equipment.

A person may suffer from the adverse effects discussed above even where only partial obstruction of the airway occurs. Partial obstruction of the airway typically results in shallow breathing referred to as a hypopnea. Other types of disordered breathing include upper airway resistance syndrome (UARS) and vibration of the airway, such as vibration of the pharyngeal wall, commonly referred to as snoring. It is also known that snoring can accompany closure of the airway leading to UARS, hypopnea, or apnea. Thus, snoring serves as an indicator that the patient is experiencing abnormal breathing.

Milder cases of disordered breathing may be treated using an oral appliance such as a mandibular advancement device (MAD). A MAD is generally structured to pull a patient's lower jaw (mandible) forward relative to their upper jaw (maxilla), which in turn, opens the patient's airway. While MADs can be very effective, they can also lead to discomfort even if used correctly due to the protrusion of the lower jaw. This is particularly problematic in the morning, when the MAD is removed and the jaws have to readjust to a normal position. This process can take several minutes and is sometimes facilitated by an appropriate tool.

Figure 1:
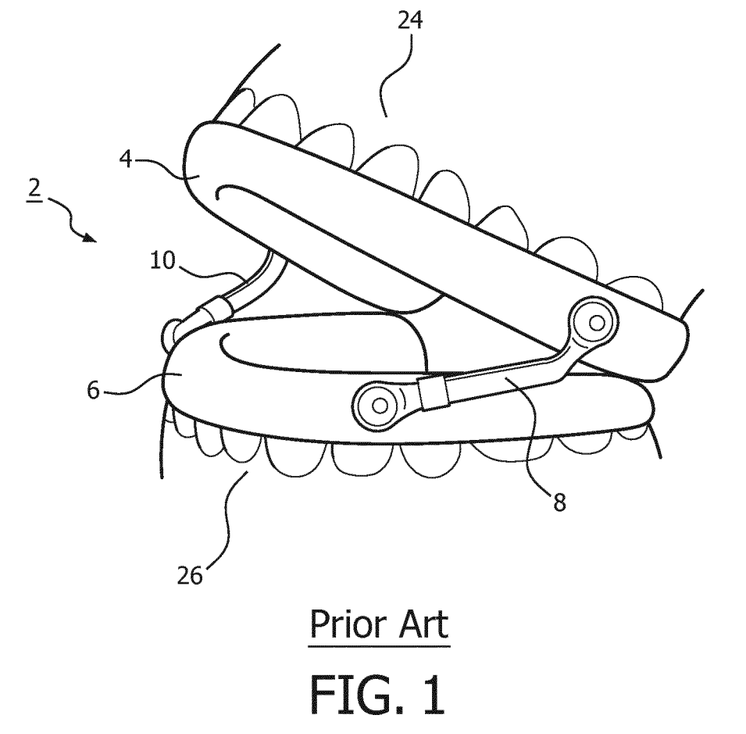
FIG. 1 is an isometric view of a prior art mandibular advancement device.

For example, FIG. 1 shows a prior art MAD 2. MAD 2 includes a first brace member 4, a second brace member 6, and a number of coupling assemblies 8,10 each coupling first brace member 4 and second brace member 6 together. First brace member 4 is structured to engage an upper dentition 24 of a user and second brace member 6 is structured to engage a lower dentition 26 of a user. In order to adjust a length of coupling assemblies 8,10, and thus adjust the relative positions of second brace member 6 with respect to first brace member 4, a user is generally required to manually adjust coupling assemblies 8,10 while MAD 2 is disposed outside of the user's mouth. This is typically performed by a practitioner once, and MAD 2 subsequently does not change positions upon being placed into and out of the user's mouth. Furthermore, this process results in the user waking up in the morning with a necessary period of uncomfortable mandibular readjustment.

Accordingly, there is a need for an improved mandibular advancement device and for a method of adjusting a dimension of a coupling assembly of a mandibular advancement device.

SUMMARY OF THE INVENTION

Accordingly, it is an object of the present invention to provide an improved mandibular advancement device and a method of adjusting a dimension of a mandibular advancement device.

As one aspect of the disclosed concept, a mandibular advancement device includes a first brace member structured to engage an upper dentition of a user, a second brace member structured to engage a lower dentition of a user, and a number of coupling assemblies each coupling the first brace member to the second brace member. Each of the number of coupling assemblies includes an actuating element structured to automatically adjust a dimension of the coupling assembly. The actuating element is selected from the group consisting of a biasing element and a volume responsive material.

As another aspect of the disclosed concept, a mandibular advancement device includes a first brace member structured to engage an upper dentition of a user, a second brace member structured to engage a lower dentition of a user, and a number of coupling assemblies each coupling the first brace member to the second brace member. Each of the number of coupling assemblies includes a microcontroller and an actuating element electrically connected to the microcontroller. The microcontroller is structured to trigger the actuating element based on a predetermined time of day.

As another aspect of the disclosed concept, a method of adjusting a dimension of a coupling assembly of a mandibular advancement device is provided. The mandibular advancement device includes a first brace member structured to engage an upper dentition of a user, a second brace member structured to engage a lower dentition of a user, and the coupling assembly coupling the first brace member to the second brace member. The method includes the steps of detecting a signal of a predetermined time of day with a microcontroller of the coupling assembly, and triggering an actuating element of the coupling assembly with the microcontroller in order to adjust the dimension of the coupling assembly.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As employed herein, the term "volume responsive material" shall mean a material that expands or contracts, in terms of volume, upon engagement with another material. A non-limiting example of a volume responsive material is a biocompatible hydrogel that is structured to expand upon engagement with a material such as, for example, saliva. A suitable non-limiting example of a hydrogel material is Poly(N-isopropylacrylamide) (PNIPAM), manufactured and distributed by Sigma-Aldrich, having its corporate offices located in St. Louis, Missouri.

As employed herein, the term "unidirectional membrane" shall mean a membrane that allows higher mobility of a molecule in one direction, compared to an opposite direction. An example of such a membrane for water transport in a preferred direction may include a hydrophilic surface on a water uptake part (i.e. an outer side) for attracting water molecules, and a hydrophobic surface on a water retention side (i.e. an inner side). A suitable non-limiting example of a unidirectional membrane is a Polysulfone Membrane, manufactured and distributed by Pall Corporation, headquartered in Port Washington, New York.

As employed herein, the phrase "predetermined time of day" shall mean a fixed time in a day that is set by a user in advance of that time when the user is awake.

As employed herein, the term "microcontroller" shall mean a suitable processing device and a memory that is provided as part of the processing device or that is operatively coupled to the processing device, and that provides a tangible storage medium for data and software routines executable by the processing device for performing controlling operations.

Directional phrases used herein, such as, for example and without limitation, left, right, upper, lower, front, back, on top of, and derivatives thereof, relate to the orientation of the elements shown in the drawings and are not limiting upon the claims unless expressly recited therein.

Figure 2A:
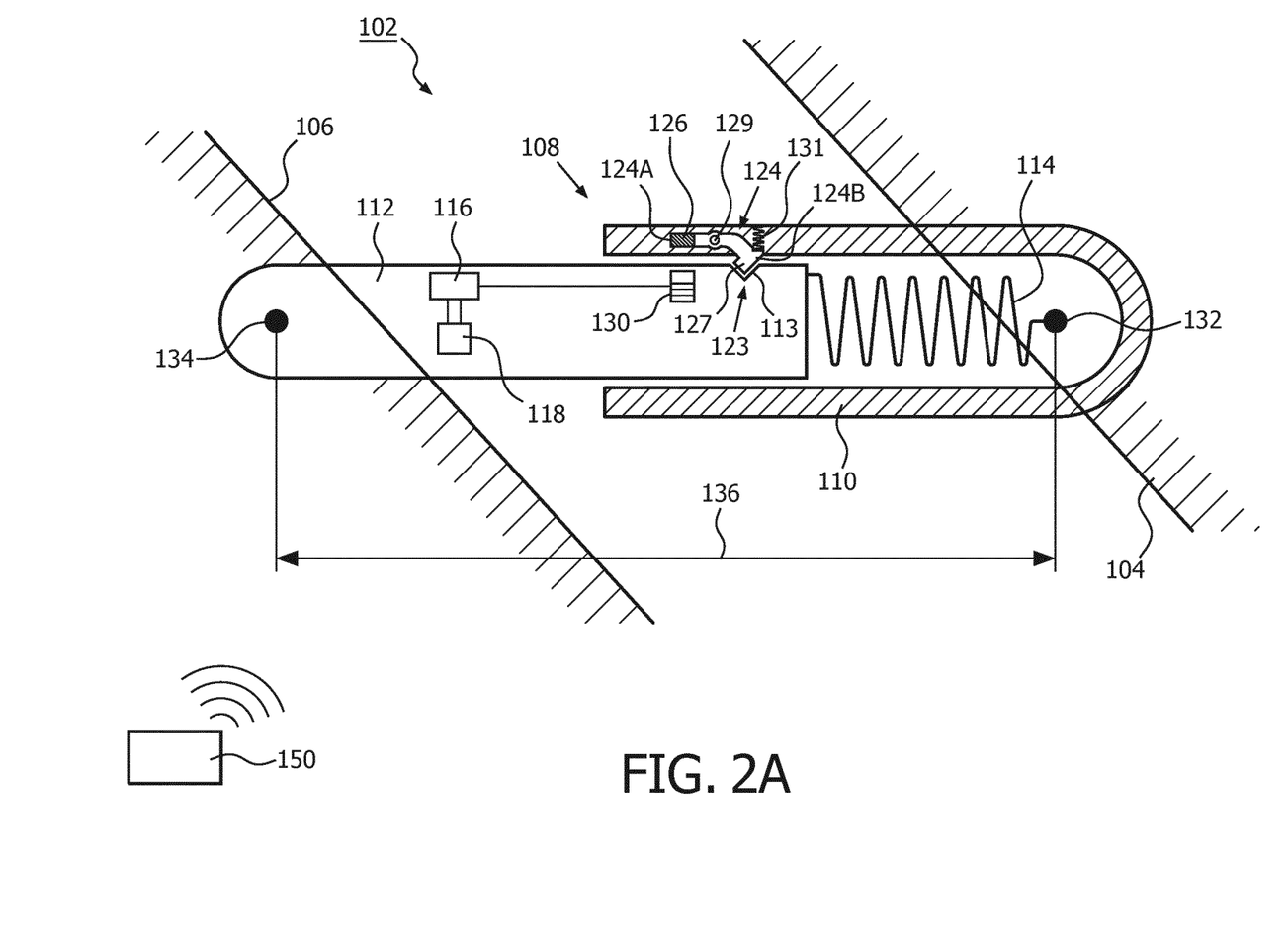
FIG. 2A is a schematic, partially sectional, view of a portion of a mandibular advancement device and coupling assembly therefor, shown in a first position, in accordance with a non-limiting embodiment of the disclosed concept.

FIG. 2A is a schematic, partially sectional, view of a MAD 102, in accordance with a non-limiting embodiment of the disclosed concept. MAD 102 includes a first brace member 104 structured to engage an upper dentition of a user, a second brace member 106 structured to engage a lower dentition of a user, and a number of coupling assemblies 108 each coupling first brace member 104 to second brace member 106 via suitable pivotable couplings (e.g., without limitation, spherical joints, hinge joints). Although only one coupling assembly 108 is shown in the example of FIG. 2A, it will be appreciated that in a preferred embodiment, MAD 102 has a second, additional coupling assembly, substantially the same as coupling assembly 108. Coupling assembly 108 includes a first coupling element 110, a second coupling element 112 partially extending into first coupling element 110, an actuating element (e.g., without limitation, a biasing element such as a spring 114), a microcontroller 116, a battery 118 for powering microcontroller 116, and an operating assembly 123 electrically connected to microcontroller 116. In one example embodiment, spring 114 is coupled to second coupling element 112 and a pivot point 132 of MAD 102, although it will be appreciated that in alternative embodiments, spring 114 can merely engage second coupling element 112 and pivot point 132 without being coupled thereto.

Operating assembly 123 includes a lever 124 having a first end 124A and an opposite second end 124B. Lever 124 is pivotally coupled to first coupling element at a pivot point 129 between first end 124A and second end 124B. Lever 124 includes a permanent magnet 126 disposed generally at or about first end 124A and a hooked portion 127 formed at or about second end 124B. Operating assembly 123 further includes an electromagnet 130 positioned on, and coupled to, second coupling element 112 such that a magnetic field produced by electromagnet 130 interacts with permanent magnet 126 as will be discussed further below.

First coupling element 110 is coupled to first brace member 104 at a first pivot point 132 and second coupling element 112 is coupled to second brace member 106 at a second pivot point 134. Microcontroller 116, battery 118, and electromagnet 130 are coupled to second coupling element 112. Battery 118 is electrically connected to microcontroller 116 and electromagnet 130 is electrically connected to microcontroller 116. Permanent magnet 126 is coupled to first coupling element 110, and operating assembly 123 further includes a biasing element (e.g., without limitation, spring 131) also coupled to first coupling element 110. Permanent magnet 126 is structured to be magnetically attracted to electromagnet 130 when electromagnet 130 is energized. As shown in FIG. 2A, second coupling element 112 includes a notched portion 113 and lever 124 is engaged with notched portion 113. In this first position, the engagement between notched portion 113 and lever 124 maintains coupling assembly 108 such that the user's lower jaw will remain protruded during therapy. Furthermore, in one example embodiment spring 131 is coupled to hook portion 127 and biases hook portion 127 toward engagement with second coupling element 112 during therapy.

Figure 2B:
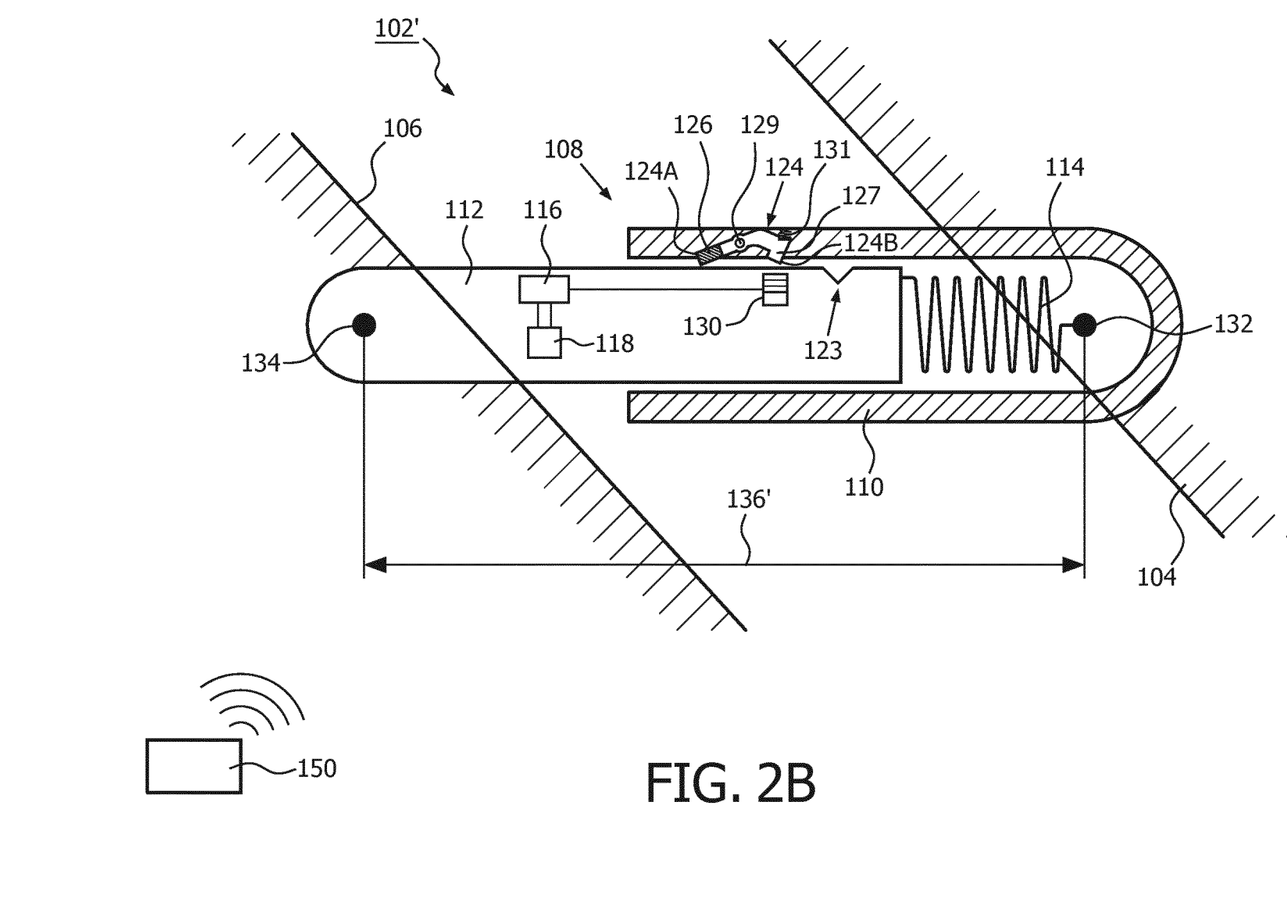
FIG. 2B is a schematic, partially sectional, view of the portion of the mandibular advancement device and coupling assembly therefor, shown in a second position.

In accordance with an embodiment of the disclosed concept, a dimension (i.e., a distance or a length) of coupling assembly 108 is structured to be automatically adjusted (i.e., changed) in order to substantially reduce any mandibular readjustment that occurs when a user awakens in the morning. Specifically, FIG. 2A shows MAD 102 in a first, treatment position (i.e., advanced position such that the lower jaw of the user will be protruded, shown in FIG. 2A) prior to being inserted into the user's mouth. A version of MAD 102 of FIG. 2A in a second position is illustrated as MAD 102' in FIG. 2B, which corresponds to a retracted position (shown in FIG. 2B). In one example embodiment, the change of positions preferably occurs at a predetermined time of day before the user wakes up in the morning. Accordingly, distinct from MAD 2 (FIG. 1), MAD 102 allows a user to awaken in the morning with his or her jaw in substantially the same position as it normally is during the day when a MAD device is not worn, thereby substantially reducing any uncomfortable mandibular readjustment in the morning. MAD 102 achieves this advantage by automatically adjusting the dimension of coupling assembly 108, or changing the length of coupling assembly 108, at a predetermined time of day before the user desires to awaken, such that when the user does awaken, the user's jaw is already in its normal position (i.e., the lower jaw is not protruded).

Operating assembly 123 is structured to move between the first position (FIG. 2A) and the second position (FIG. 2B) in order to automatically adjust a dimension (e.g., without limitation, a distance 136) between pivot points 132,134. This advantageously provides more comfort and relaxation to a user when MAD 102 is removed in the morning. In one embodiment, distance 136 in FIG. 2A is greater than a distance 136' in FIG. 2B. In this manner, when first distance 136 is shortened to second distance 136', the user's lower jaw is no longer protruded with respect to the user's upper jaw.

In order to achieve this desired benefit, an external controller 150 (e.g., without limitation, a cell phone, a wake-up light, an alarm clock, and/or a home monitoring hub) is provided. External controller 150 may either send a wireless signal to microcontroller 116 at a predetermined time of day pre-set by a user (i.e., several minutes before the user desires to wake up), or may send a wireless signal to microcontroller 116 in advance of a set time at which microcontroller 116 is to energize electromagnet 130. Accordingly, when microcontroller 116 is activated by external controller 150, microcontroller 116 energizes electromagnet 130. As a result, there is a magnetic attraction between electromagnet 130 and permanent magnet 126, which causes lever 124 to rotate about pivot point 129 (i.e., counter-clockwise in the example shown in FIG. 2A) and thus cause second end 124B to move away from, and disengage from, notched portion 113. Furthermore, with second end 124B of lever 124 no longer engaging notched portion 113, spring 114 is free to move second coupling element 112 independently (i.e., move second coupling element toward pivot point 132) with respect to first coupling element 110 in order to automatically adjust distance 136 when operating assembly 123 moves from the first position (i.e., corresponding to engagement between notched portion 113 and lever 124) to the second position (i.e., corresponding to disengagement between notched portion 113 and lever 124).

Preferably, this change of positions of operating assembly 123 occurs at a predetermined time of day before the user desires to awaken (i.e., several minutes beforehand), so that maximum therapy can be realized and the user can still awaken with a jaw in the position that it is during the day when MAD 102 is not being worn. While the disclosed embodiment has been described herein in association with operating assembly 123, it will be appreciated that any suitable alternative operating assembly may be employed with spring 114 in order to perform the desired function of automatically adjusting distance 136 at a predetermined time of day before the user awakens. It will also be appreciated that in a suitable alternative embodiment, spring 114 can function as a damper, rather than as an actuating element, such that releasing of lever 124 allows the user's jaws to naturally readjust without requiring any pulling of spring 114.

Figure 5:
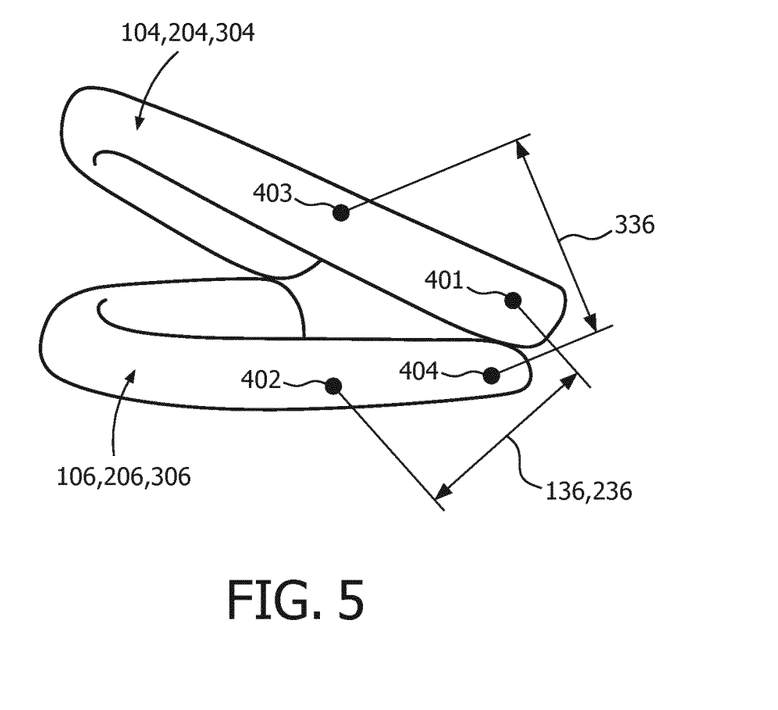
FIG. 5 is a schematic view of a first brace member and a second brace member for a mandibular advancement device.

FIG. 5 shows a schematic view of first brace member 104 and second brace member 106. It will be appreciated that in the disclosed example embodiment, pivot points 132,134 (FIG. 2A) correspond to location 401 on first brace member 104 and location 402 on second brace member 106, respectively. As such, distance 136 shortens when MAD 102 moves from the first position (FIG. 2A) to the second position (FIG. 2B) in order to provide the aforementioned advantages. It will however be appreciated that in an alternative embodiment, similar suitable alternative pivot points for a similar MAD could correspond to location 403 on first brace member 104 and location 404 on second brace member 106, respectively. In such an alternative embodiment, an actuating element (e.g., without limitation, a biasing element such as a spring) would be structured to lengthen a distance when the MAD moved between positions, in order to allow a user to awaken with his or her jaw in a non-treatment position.

Figure 3:
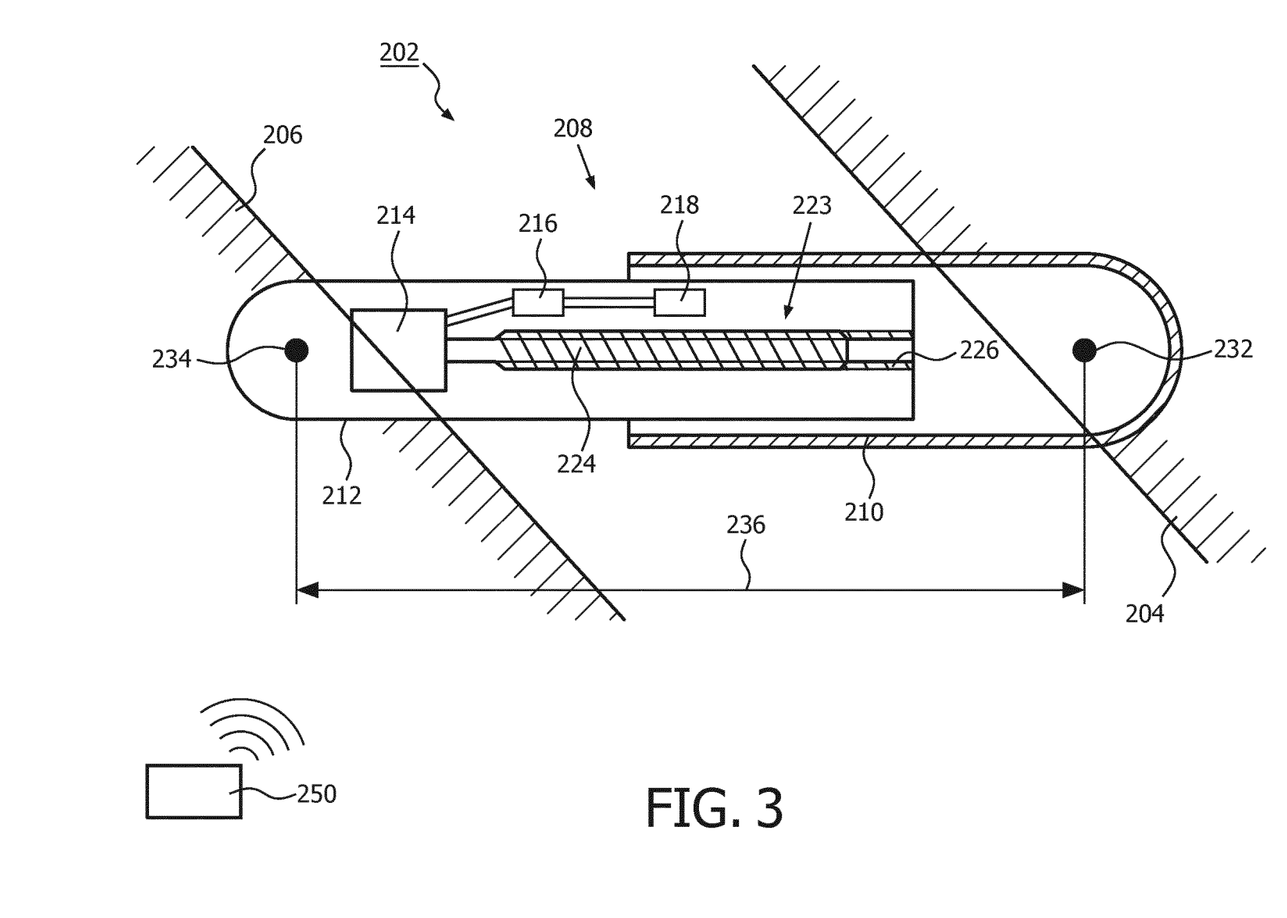
FIG. 3 is a schematic, partially sectional, view of a portion of another mandibular advancement device and coupling assembly therefor, in accordance with another non-limiting embodiment of the disclosed concept.

FIG. 3 is a schematic, partially sectional, view of another novel MAD 202, in accordance with another non-limiting embodiment of the disclosed concept. Similar to MAD 102 (FIG. 2A), MAD 202 includes first and second brace members 204,206 that are structured to engage upper and lower dentitions of a user, and a number of coupling assemblies (only one coupling assembly 208 is shown in the example of FIG. 3) each coupling first brace member 204 to second brace member 206. However, coupling assembly 208 is different than coupling assembly 108 (FIG. 2A). Coupling assembly 208 includes a first coupling element 210, a second coupling element 212 partially extending into first coupling element 210, an actuating element (e.g., without limitation, electric motor 214), a microcontroller 216 electrically connected to electric motor 214, a battery 218 for powering microcontroller 216, and an operating assembly 223 electrically connected to microcontroller 216 and being structured to couple first coupling element 210 to second coupling element 212.

First coupling element 210 is coupled to first brace member 204 at a first pivot point 232, second coupling element 212 is coupled to second brace member 206 at a second pivot point 234. Operating assembly 223 includes a threaded spindle 224 coupled to electric motor 214, and a threaded tube 226 coupled to first coupling element 210. As shown in FIG. 3, threaded spindle 224 extends into and is threadably engaged with threaded tube 226. Microcontroller 216 is electrically connected to electric motor 214 and microcontroller 216 is further electrically connected to battery 218. Similar to operating assembly 123 (FIG. 2A), operating assembly 223 is structured to move between first and second positions in order to automatically adjust a dimension (i.e., a distance or a length 236 between pivot points 232,234) of coupling assembly 208. That is, in one example embodiment, operating assembly 223 is structured to automatically shorten distance 236 from a first length to a second, shorter length, at a predetermined time of day before a user awakens, such that maximum therapy can be realized, and the user can awaken with his or her jaw already in a normal position as when MAD 202 is not being worn.

In order to achieve this desired benefit, an external controller 250 (e.g., without limitation, a cell phone, a wake-up light, an alarm clock, and/or a home monitoring hub) is provided and is structured to send a wireless signal to microcontroller 216 either at a predetermined time of day pre-set by a user (i.e., several minutes before the user desires to wake up), or may send a wireless signal to microcontroller 216 in advance of a set time at which microcontroller 216 is to trigger electric motor 214. As a result, electric motor 214 drives operating assembly 223 in order to automatically adjust distance 236. That is, electric motor 214 causes threaded spindle 224 to rotate within threaded tube 226, thereby shortening distance 236. Stated differently, when electric motor 214 causes threaded spindle 224 to rotate within threaded tube 226, threaded spindle 224 pulls first coupling element 210 toward pivot point 234 in order to shorten distance 236 from a first length to a second, shorter length, and provide the same benefits as MAD 102. While the disclosed embodiment has been described herein in association with operating assembly 223, it will be appreciated that any suitable alternative operating assembly may be employed with electric motor 214 in order to perform the desired function of automatically adjusting distance 236 at a predetermined time of day before the user awakens. For example and without limitation, electric motor 214 could be combined with a pinion and gear rack (not shown) coupled to either first brace member 204 or second brace member 206.

Additionally, while MAD 202 is able to move between positions at a predetermined time of day just before a user wakes up in the morning, MAD 202 is also able to move from the second position (non-treatment) to the first position (treatment position) after the user has inserted MAD 202 and has fallen asleep. In this manner, the user can fall asleep while MAD 202 is still in a natural, non-treatment position. Accordingly, MAD 202 in such an embodiment would be required to be coupled to a sensor (e.g., without limitation, a fitness tracker, not shown) in order to detect the sleep phase of the user.

FIG. 5 shows first brace member 204 and second brace member 206. It will be appreciated that in the disclosed example embodiment, pivot points 232,234 (FIG. 3) correspond to location 401 on first brace member 204 and location 402 on second brace member 206, respectively. As such, distance 236 shortens when MAD 202 moves from the first position (FIG. 3) to the second position in order to provide the aforementioned advantages. It will however be appreciated that in an alternative embodiment, similar suitable alternative pivot points for a similar MAD could correspond to location 403 on first brace member 204 and location 404 on second brace member 206, respectively. In such an alternative embodiment, operating assembly 223 would be structured to lengthen a distance when the MAD moved between positions, in order to allow a user to awaken with his or her jaw in a non-treatment position.

It will be appreciated that a method of adjusting a dimension 136,236 of a coupling assembly 108,208 of a MAD 102,202 includes the steps of detecting a signal of a predetermined time of day with a microcontroller 116,216, and triggering an actuating element 114,214 with microcontroller 116,216 in order to adjust dimension 136,236. The method may also include the step of sending a wireless signal to microcontroller 116,216 with an external controller 150,250 in order to trigger actuating element 114,214.

Figure 4:
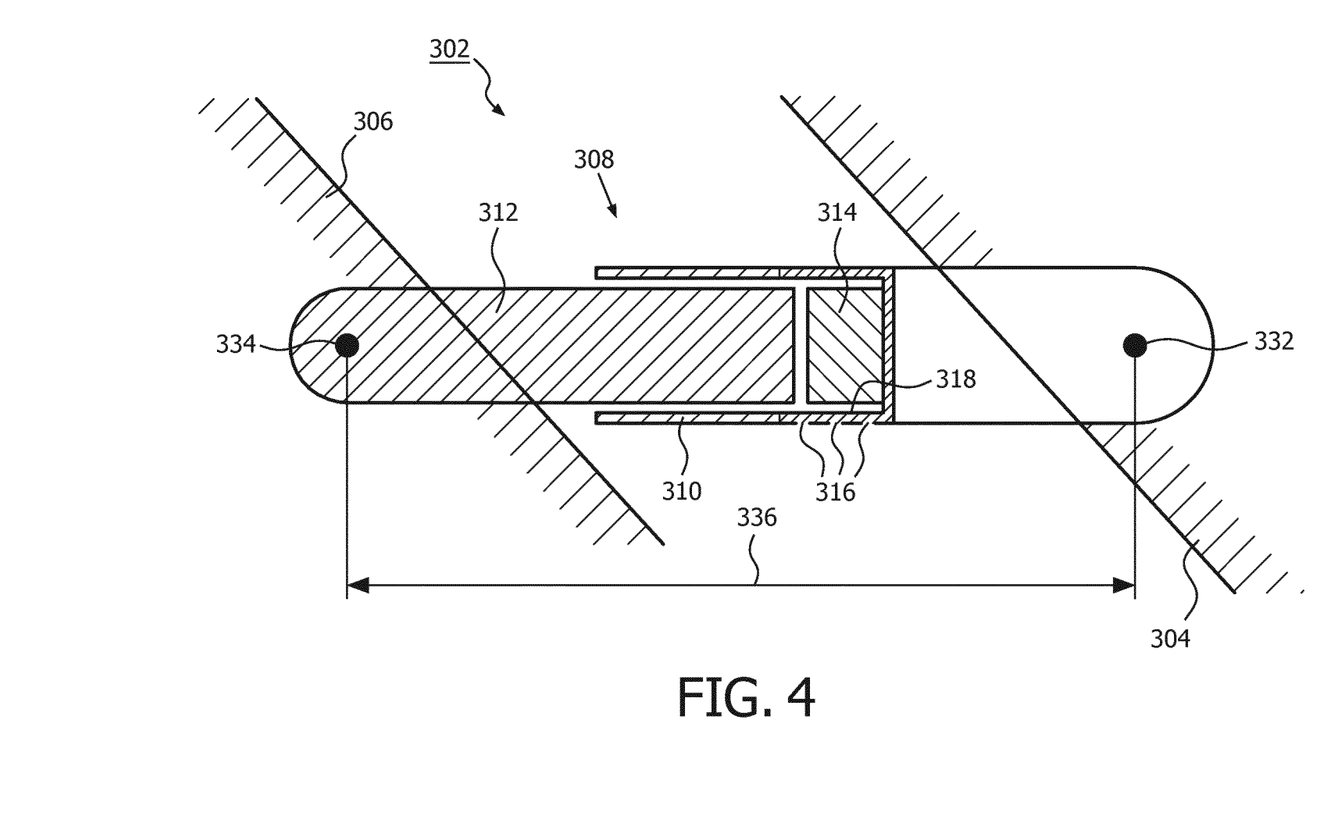
FIG. 4 is a schematic, partially sectional, view of a portion of another mandibular advancement device and coupling assembly therefor, in accordance with another non-limiting embodiment of the disclosed concept.

FIG. 4 shows a schematic, partially sectional, view of another MAD 302, in accordance with another non-limiting embodiment of the disclosed concept. MAD 302 is structured similar to MADs 102,202 (FIGS. 2A and 3), including first and second brace members 304,306 that are structured to engage upper and lower dentitions of a user, but MAD 302 has an actuating element (e.g., without limitation, a volume responsive material 314) that automatically adjusts a corresponding distance 336 of a coupling assembly 308 gradually, rather than at a predetermined time of day. Specifically, coupling assembly 308 includes first and second coupling elements 310,312 coupled to first and second brace members 304,306 at respective pivot points 332,334, and volume responsive material 314 is located between and engages each of coupling elements 310,312. As shown in FIG. 4, first coupling element 310 has a number of perforations 316, and it will be appreciated that coupling assembly 308 further has a unidirectional membrane 318 located in and being coupled to an interior of first coupling element 310.

In one example embodiment, when MAD 302 is donned by a user, volume responsive material 314 is structured to expand in order to move (i.e., press against and push) second coupling element 312 independently with respect to first coupling element 310. That is, volume responsive material 314 moves second coupling element 312 away from pivot point 332. More specifically, this arrangement allows saliva from the user to pass through perforations 316 and unidirectional membrane 318 in order to contact and cause volume responsive material 314 to expand. As a result, distance 336 lengthens from a first length to a second, longer length. It will be appreciated that throughout the course of a treatment period (i.e., throughout the night), as volume responsive material 314 expands, it will cause second coupling element 312 to return to its pre-therapy position and thereby allow the user to awaken with his or her jaw in substantially the same position as it normally is without MAD 302. Thus, problems associated with a jaw having a readjustment period in the morning after a MAD is taken out are substantially reduced when a user dons MAD 302.

Furthermore, during the day, when MAD 302 is not donned by the user, volume responsive material 314 is structured to be dried in order to contract and return MAD 302 to a "therapy-ready" position. Drying MAD 302 can be achieved by, for example and without limitation, storing MAD 302 in dry conditions, in a desiccator (not shown), and/or by means of a chemical driven process for altering the water binding behavior within the material network of volume responsive material 314. Regarding MADs 102,202 (FIGS. 2A and 3), batteries 118,218 (FIGS. 2A and 3) can be recharged wirelessly during the day when MADs 102,202 (FIGS. 2A and 3) are not donned, for example and without limitation, by placing MADs 102,202 (FIGS. 2A and 3) in a wireless charging station (not shown) or by connecting them to cable-based chargers (not shown).

FIG. 5 shows first brace member 304 and second brace member 306. It will be appreciated that in the disclosed example embodiment, pivot points 332,334 (FIG. 4) correspond to location 403 on first brace member 304 and location 404 on second brace member 306, respectively. Accordingly, distance 336 lengthens when MAD 302 (FIG. 4) moves from the first position to the second position to provide the aforementioned advantages.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A mandibular advancement device comprising: a first brace member structured to removably engage an upper dentition of a user; a second brace member structured to removably engage a lower dentition of the user; and two coupling assemblies interconnected between points on opposite outer sides of the first brace member and the second brace member, wherein each coupling assembly includes an actuating element interconnected between a first point on the first brace member and a second point on the second brace member and that comprises a volume responsive material structured to actively adjust a dimension of the respective coupling assembly gradually, via the volume responsive material, over a period of time corresponding to a portion of a day or 24-hour period, from a first length to a second, longer length and back again to the first length, wherein the first length corresponds with a therapy-ready protruded position of the mandibular advancement device in which each of the coupling assemblies is configured, at a start of a treatment period within the portion of the day or 24-hour period, to protrude the second brace member with respect to the first brace member away from a normal non-adjusted, non-protruded, positioning of the lower dentition with respect to the upper dentition when a user's intraoral saliva increasingly passes through perforations of a first coupling element and then through a unidirectional membrane coupled on an interior surface of the first coupling element and then into the volume responsive material which causes the volume responsive material to expand; and the second, longer length corresponds with a treatment position of the mandibular advancement device that comprises a retracted position in a direction opposite the therapy-ready protruded position, subsequent to the start of the treatment period and until the end of the treatment period, in which each coupling assembly is configured to no longer protrude the second brace member with respect to the first brace member in the therapy-ready protruded position, but to bias the second brace member with respect to the first brace member in the direction of the retracted position away from the therapy-ready protruded position until reaching the normal non-adjusted, non-protruded, positioning of the lower dentition with respect to the upper dentition at the end of the treatment period when the user's intraoral saliva that passes through the perforations of the first coupling element and through the unidirectional membrane and into the volume responsive material is below a threshold intake which causes the volume responsive material to retract.

2. The mandibular advancement device according to claim 1, wherein each coupling assembly further comprises the first coupling element and a second coupling element partially extending into the first coupling element; wherein the first coupling element is coupled to the first brace member at a first pivot point; wherein the second coupling element is coupled to the second brace member at a second pivot point; and wherein the dimension is a distance between the first pivot point and the second pivot point.

3. The mandibular advancement device according to claim 2 wherein the volume responsive material is structured to engage each of the first coupling element and the second coupling element and to expand or contract in order to actively move the second coupling element independently with respect to the first coupling element.

4. The mandibular advancement device according to claim 3, wherein the volume responsive material is a hydrogel.

* * * * *